United States Patent
Takahashi et al.

(10) Patent No.: US 7,847,249 B2
(45) Date of Patent: Dec. 7, 2010

(54) CHARGED PARTICLE BEAM APPARATUS

(75) Inventors: Noritsugu Takahashi, Kokubunji (JP); Muneyuki Fukuda, Kokubunji (JP); Hiroyuki Ito, Hitachinaka (JP); Atsuko Fukada, Kokubunji (JP); Masashi Sakamoto, Hitachinaka (JP); Satoshi Takada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 299 days.

(21) Appl. No.: 12/068,417

(22) Filed: Feb. 6, 2008

(65) Prior Publication Data

US 2008/0185519 A1 Aug. 7, 2008

(30) Foreign Application Priority Data

Feb. 7, 2007 (JP) ............... 2007-027488

(51) Int. Cl.
 *H01J 3/14* (2006.01)
(52) U.S. Cl. ............ 250/310; 250/311; 250/396 R; 250/396 ML; 250/492.1; 250/492.22; 250/491.1
(58) Field of Classification Search ............ None
 See application file for complete search history.

(56) References Cited

U.S. PATENT DOCUMENTS

| | | | | |
|---|---|---|---|---|
| 5,216,235 A | | 6/1993 | Lin | |
| 5,526,165 A | * | 6/1996 | Toda et al. | 359/202.1 |
| 5,578,821 A | * | 11/1996 | Meisberger et al. | 250/310 |
| 5,598,002 A | * | 1/1997 | Todokoro et al. | 250/310 |
| 5,717,204 A | * | 2/1998 | Meisburger et al. | 250/310 |
| 5,835,251 A | * | 11/1998 | Toda et al. | 359/198.1 |
| 6,946,656 B2 | * | 9/2005 | Ezumi et al. | 850/11 |
| 7,049,585 B2 | * | 5/2006 | Nakasuji et al. | 250/310 |
| 7,087,899 B2 | * | 8/2006 | Ezumi et al. | 250/311 |
| 7,109,484 B2 | * | 9/2006 | Nakasuji et al. | 250/310 |
| 7,372,028 B2 | * | 5/2008 | Ezumi et al. | 250/310 |
| 7,417,236 B2 | * | 8/2008 | Nakasuji et al. | 250/440.11 |
| 2005/0092921 A1 | * | 5/2005 | Nakasuji et al. | 250/306 |
| 2005/0161600 A1 | * | 7/2005 | Ezumi et al. | 250/310 |
| 2006/0219918 A1 | * | 10/2006 | Ezumi et al. | 250/311 |
| 2008/0100832 A1 | * | 5/2008 | Sato et al. | 356/237.5 |
| 2009/0032722 A1 | * | 2/2009 | Ito et al. | 250/396 R |

FOREIGN PATENT DOCUMENTS

JP 08-096738 9/1994

* cited by examiner

*Primary Examiner*—David A Vanore
(74) *Attorney, Agent, or Firm*—Stites & Harbison, PLLC; Juan Carlos A. Marquez, Esq

(57) ABSTRACT

A technology whereby removal of magnetic hysteresis is enabled in short time in parallel with a process for stage transfer, and so forth. There is executed a magnetic hysteresis removal sequence whereby current for exciting an electromagnetic coil prior to acquisition of an image is always set to a predetermined variation value against a target value, thereby obtaining information on an image, and so forth, when a diameter of a primary electron beam, converged on the specimen, becomes smaller than dimensions displayed by one pixel of an image to be acquired.

18 Claims, 11 Drawing Sheets

FIG. 2
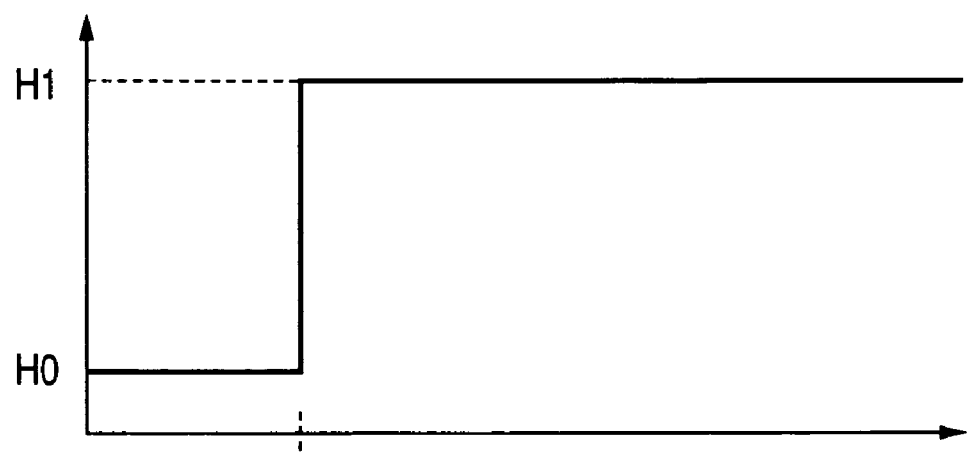
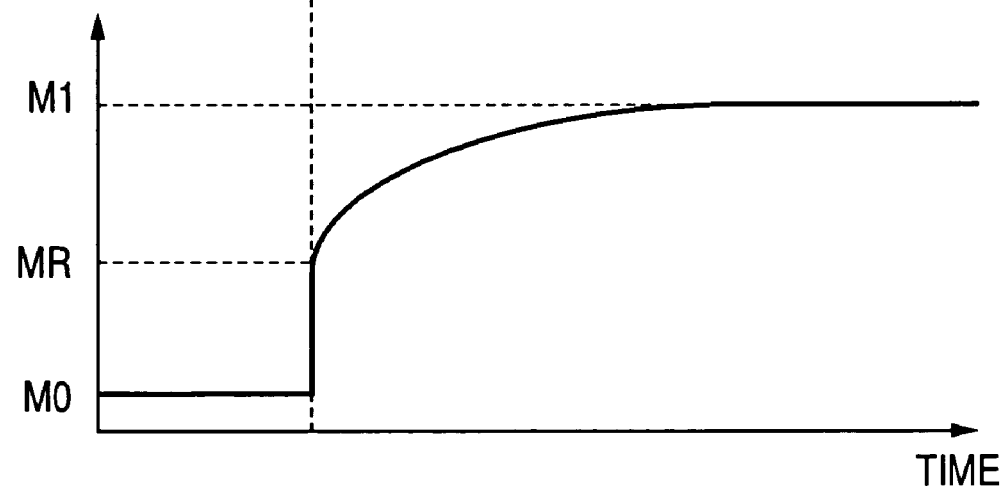

CHARGED PARTICLE BEAM APPARATUS

CLAIM OF PRIORITY

The present application claims priority from Japanese application JP 2007-027488 filed on Feb. 7, 2007, the content of which is hereby incorporated by reference into this application.

FIELD OF THE INVENTION

The invention relates to a charged particle beam apparatus using a charged particle beam such as an electron beam, an ion beam, and so forth.

BACKGROUND OF THE INVENTION

A charged particle beam apparatus is an apparatus for obtaining a specimen image by use of a signal generated from a specimen by scanning on the specimen with a thinly focused charged particle beam. With a charged particle beam apparatus for use in testing a photomask, and a wafer, to be used in a semiconductor process, in particular, among charged particle beam apparatuses, it is necessary to acquire information such as an image, and so forth, at high speed in order to enhance throughput per unit of time. In focusing of a charged particle beam, use is normally made of a magnetic lens employing an electromagnetic coil. However, in the case of using the magnetic lens, there occurs deterioration in repeatability of a magnetic field produced by the magnetic lens due to an effect of magnetic hysteresis occurring to a magnetic material of the magnetic lens even if current of the electromagnetic coil is set the coincident condition. Accordingly, even if an excitation current of the magnetic lens is set to an excitation condition of the magnetic lens, under which the best image without being defocused should be obtained, an image as acquired will be defocused if the repeatability undergoes deterioration. In consequence, re-adjustment of the magnetic lens is required, resulting in an increase in time length necessary for obtaining the specimen image. It follows therefore that a technology for removing the magnetic hysteresis of the magnetic lens is necessary in order to avoid the increase in the time length as required.

As to a technology for removal of the effect of magnetic hysteresis, Japanese Patent No. 3458481 has disclosed the technology for removing the effect of magnetic hysteresis by unit of executing a sequence of steps for exciting the electromagnetic coil with current at values reversed in polarity from each other, or at a maximum value and a minimum value, which can be set by the apparatus, during stage transfer, and subsequently setting to a desired current of the electromagnetic coil. Meanwhile, in U.S. Pat. No. 5,216,235, there has been disclosed the technology for focusing by varying a position of a specimen plane so as to keep a distance between an objective lens, and the specimen plane constant without changing setting of an electromagnetic coil, as a technology for avoiding a magnetic hysteresis phenomenon of the magnetic lens.

SUMMARY OF THE INVENTION

With the technology disclosed in Japanese Patent No. 3458481, the current for exciting the electromagnetic coil is set to a maximum value and a minimum value regardless of variation in energy of an electron beam with which a specimen is irradiated, and variation in distance between an objective lens, and a specimen plane. Accordingly, it takes longer time for a magnetic field to be stabilized immediately after completion of a magnetic hysteresis removal sequence, and furthermore, there occurs fluctuation in time length. As a result, effective execution time for the magnetic hysteresis removal sequence is dependent on a maximum value of a time length necessary for stabilization of the magnetic field. With the technology disclosed in U.S. Pat. No. 5,216,235, since there is the need for keeping the distance between the objective lens and the specimen plane constant all the time, a mechanism for driving a specimen stage in the direction of a beam axis is required. If a mechanism for driving in the z-axis direction is installed, this will render a specimen stage mechanically complex, requiring longer time in driving.

It is therefore an object of the invention to provide a technology capable of removal of magnetic hysteresis in short time in parallel with a process for stage transfer, and so forth.

With a charged particle beam apparatus for acquiring a charged particle beam image by irradiating a specimen with a charged particle beam, there is the case where an image acquisition speed substantially as high as a target resolution of an image is required in some instances. With any of the inventions disclosed in the documents referred to as above, an object of the invention is to set excitation conditions of a magnetic lens to conditions under which the best image without being defocused can be acquired, in other words, conditions under which imaging conditions at the time of acquiring an image allow an apparatus to maintain the highest resolution. The inventor of the present invention has found out that a magnetic hysteresis reduction process executed against magnetic lens unit installed in a charged particle beam optical system may be set with the objective of maintaining only a target resolution required of an image as acquired instead of the highest resolution, that is, there will be no problem even if a sequence of the magnetic hysteresis reduction process is stopped at a point in time when a diameter of a primary charged particle beam, on a specimen, becomes smaller than dimensions displayed by one pixel of an image to be acquired.

The basic concept of findings described as above is shown hereunder. FIG. 2 is a schematic diagram showing change over time, in magnetization of a magnetic material, in relation to an external applied magnetic field. When the external applied magnetic field is caused to undergo an instantaneous change from H0 to H1, the magnetization of the magnetic material undergoes an instantaneous change from M0 to MR, and subsequently, is asymptotically converged to M1. The magnetization of the magnetic material, asymptotically changing from MR to M1, is written as a function of variation in the external applied magnetic field, and time. Since strength of a magnetic field produced by a magnetic lens undergoes a change according to intensity of magnetization of a magnetic material used in the magnetic lens, a diameter of a spot of a primary charged particle beam condensed on a specimen after a change in current applied to an electromagnetic coil of the magnetic lens is expressed by a function of variation in the external applied magnetic field and time elapsed from a time when the external applied magnetic field is caused to change, so that it becomes possible to predict a time when the dimensions of the primary charged particle beam on a specimen becomes smaller than the dimensions of field of view per a pixel of the image to be acquired.

Thus, with the invention, it is possible to shorten time required for removal of magnetic hysteresis, and to obtain sharp acquired images all the time.

BRIEF DESCRIPTION OF THE DRAWINGS

FIG. 2 is a schematic diagram showing change over time, in magnetization of a magnetic material, in relation to an external applied magnetic field;

DETAILED DESCRIPTION OF THE PREFERRED EMBODIMENTS

Embodiments of the invention are described hereinafter with reference to the accompanying drawings. In the description of the embodiments given hereunder, "removal of magnetic hysteresis" refers to not only the case of complete removal of magnetic hysteresis but also the case of reduction of magnetic hysteresis to a given value or lower.

First Embodiment

As a first embodiment, there is described hereinafter an embodiment of a defect-review system mounted with a function for removal of magnetic hysteresis at the time of a change in conditions of an objective lens, accompanied with transfer of an observation position. The defect-review system is an apparatus for acquiring images of regions containing respective defects at high speed on the basis of information on positions of the respective defects existing on a semiconductor wafer, detected by another inspection apparatus such as a visual inspection apparatus, and so forth. A scanning electron microscope is mainly used as image acquisition unit. The number of defects, detected by the visual inspection apparatus, falls in a range of from several scores to on the order of several hundreds of pieces per unit sheet of wafer, and furthermore, execution of sequential defect reviews is required of continuously streaming semiconductor wafers on a production line of semiconductor devices. Accordingly, high-speed image acquisition as well as high-quality image acquisition is required of the defect-review system.

Figure 1:
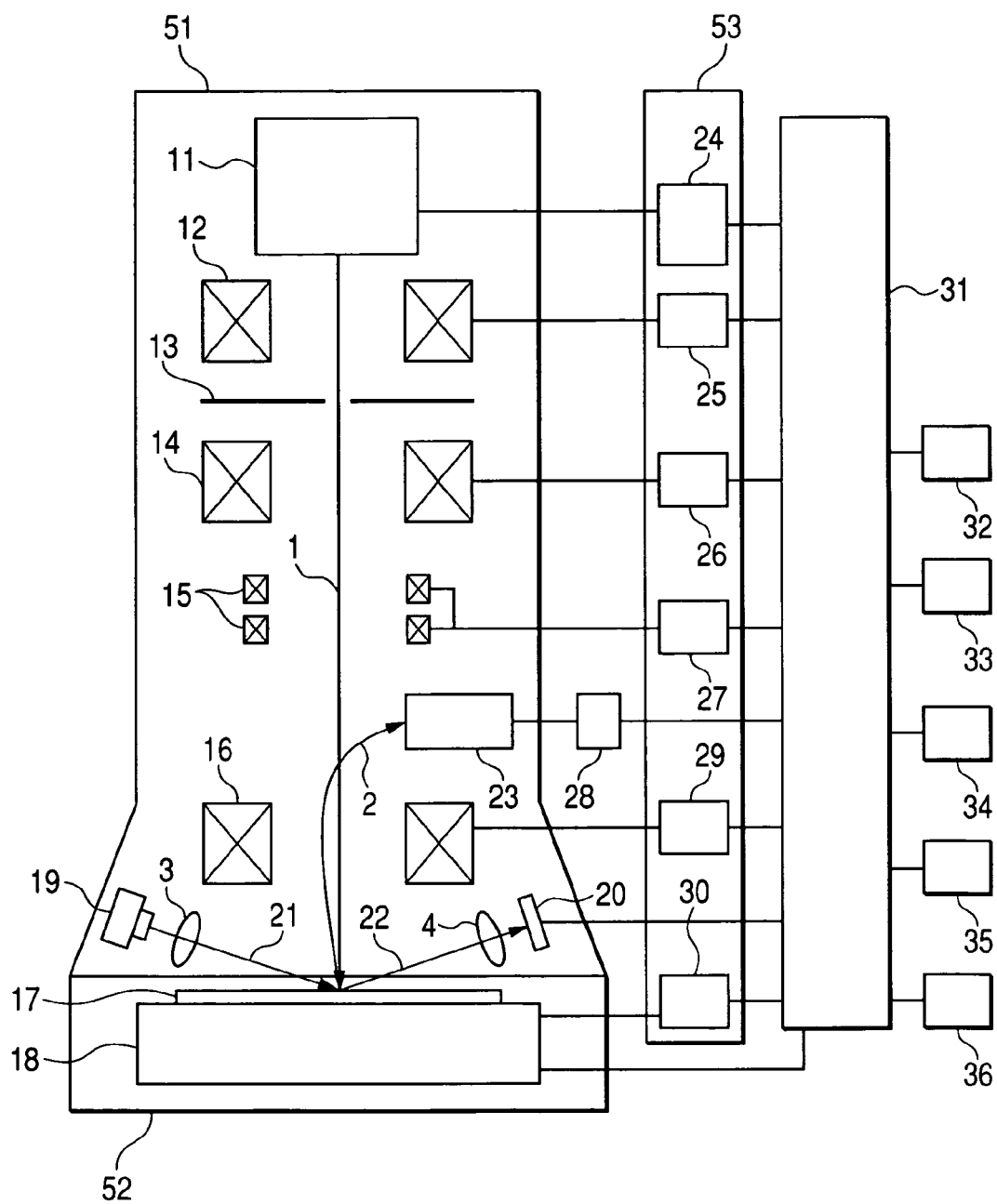
FIG. 1 is a schematic block diagram of a charged particle beam apparatus according to the invention.

FIG. 1 is a schematic block diagram of the defect-review system according to the present embodiment. The defect-review system shown in FIG. 1 comprises a scanning electron microscope made up of an electron beam column 51, and a specimen chamber 52, a power supply unit 53 for supplying various operation voltages, and drive currents inside the electron beam column 51, an operation unit 31 for executing overall control of the system in whole, and accessories of the operation unit 31 such as a display device 32, an image memory 33, a wafer information memory 34, an input unit 35, a memory 36, and so forth.

A primary electron beam 1 emitted from an electron source 11 controlled by a high-voltage control power source 24 according to an instruction of the operation unit 31 is condensed by a first condenser lens 12 controlled by a lens control power source 25 according to an instruction of the operation unit 31, whereupon unnecessary regions of the primary electron beam 1 are removed by an aperture 13, and the primary electron beam 1 is subsequently condensed into a minute spot on a specimen 17 by a second condenser lens 14 controlled by a lens control power source 26 according to an instruction of the operation unit 31, and by an objective lens 16 controlled by an objective lens control power supply source 29 according to an instruction of the operation unit 31. The primary electron beam 1 is caused to two-dimensionally scan on the specimen according to a size of a scanning region, and scanning speed by a deflector 15 controlled by a deflector control power supply source 27 according to an instruction of the operation unit 31. When a voltage controlled by a specimen control power supply source 30 is applied to the specimen 17 according to an instruction of the operation unit 31, the specimen 17 is irradiated with the primary electron beam 1 at reduced speed. A secondary signal 2 that consists of a secondary electron, and so forth, generated from the specimen 17 upon irradiation thereof with the primary electron beam 1, is detected by a secondary signal detector 23. The signal detected by the secondary signal detector 23 is amplified by a signal amplifier 28 to be subsequently transferred to the image memory 33, whereupon a specimen image is displayed on the display device 32.

A specimen stage 18 is capable of independently transferring the specimen 17 in at least two directions in a plane perpendicular to an incident direction of the primary electron beam 1. Further, the specimen stage 18 is capable of reading coordinates of an observation position, stored in the wafer information memory 34, or coordinates inputted in the input unit 35 to thereby transfer the specimen 17 according to an instruction of the operation unit 31. A distance between the objective lens 16 and the specimen 17 is measured by a Z-sensor. With the Z-sensor, an incident light 3 emitted from a light source 19 passes through an optical lens 21 to then irradiate on the specimen 17, and subsequently, a reflected light 4 passing through an optical lens 22 is detected by a light position detector 20, thereby measuring the distance between the objective lens 16, and the specimen 17.

The power supply unit 53 is a set of the control power supply sources for respective constituent components of the electron beam column 51, and the specimen stage 18, the power supply unit 53 comprising the high-voltage control power source 24, the lens control power sources 25, 26, the deflector control power supply source 27, the objective lens control power supply source 29, the specimen control power supply source 30 for applying a deceleration electric field to the specimen stage 18, and so forth.

Unless there is a change in conditions of a lens system except the objective lens 16, a current value of the objective lens 16, for causing the primary electron beam 1 to form a spot optimum in diameter on the specimen 17, is directly and exclusively dependent on the distance between the objective lens, and the specimen. Accordingly, the operation unit 31 can work out a current value of the objective lens 16, for causing the primary electron beam 1 to form a minimum spot on the specimen 17, on the basis of a measured value of the distance between the objective lens 16, and the specimen 17, thereby instructing the objective lens control power supply source 29 to control so as to apply the measured value as worked out. Set values concerning a magnetic hysteresis removal sequence of the objective lens, and a formula for working out the set values are stored in the memory 36. The operation unit 31 can read information on the magnetic hysteresis removal sequence from the memory 36, thereby setting a current value and current-holding time of the objective lens, and a degauss-completion time by use of information obtained by computation with the formula.

Figure 3:
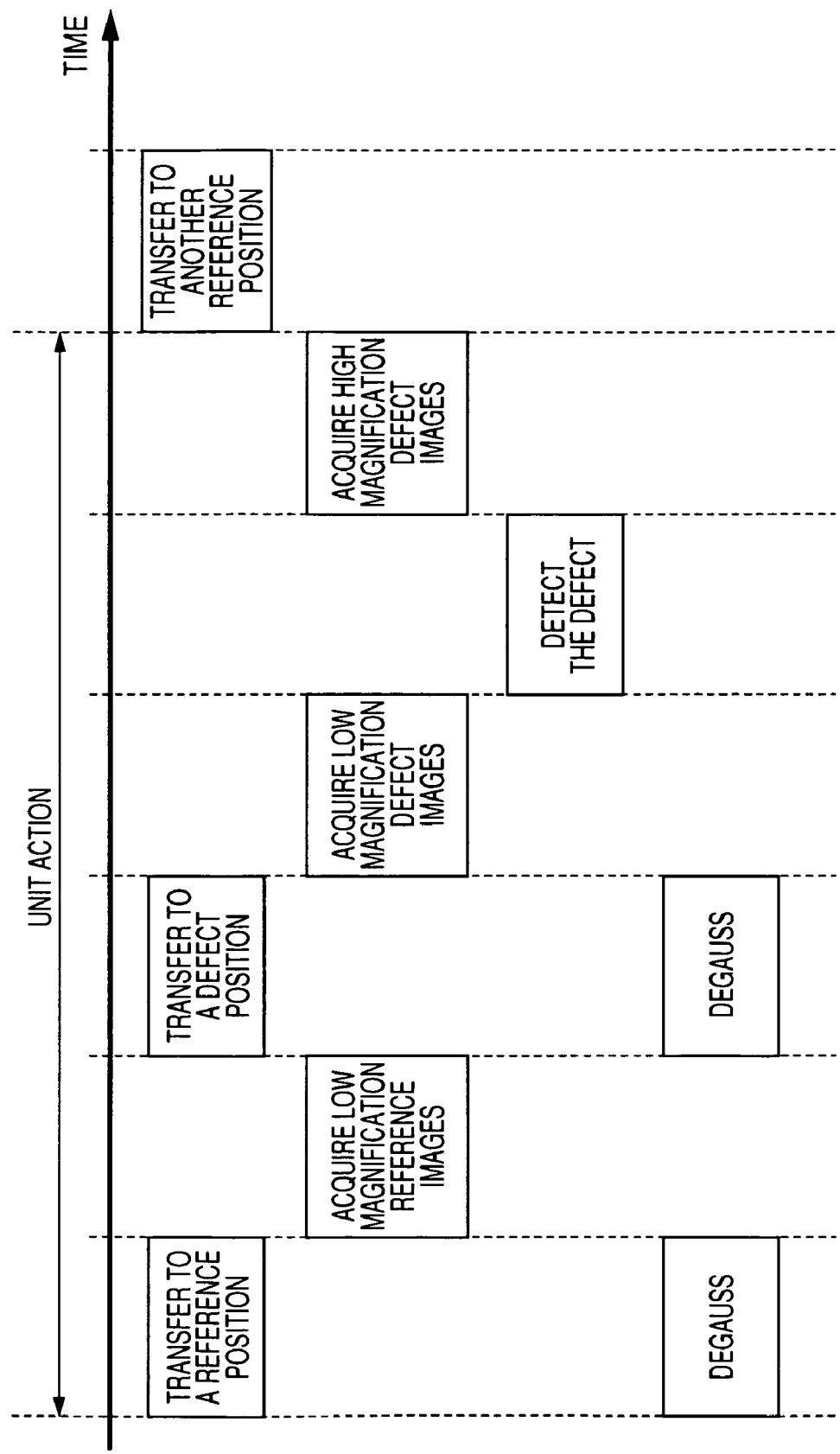
FIG. 3 shows an operation flow of a defect-review system according to the invention.

FIG. 3 shows an overall operation flow of the defect-review system. With the defect-review system according to the present embodiment, there is executed a sequence of unit actions on each of defect-positions, each of the unit actions comprising the steps of transfer to a reference position→acquisition of a low magnification reference image→transfer to a defect position→acquisition of a low magnification defect image→defect the defect→acquisition of a high magnification defect image. The sequence of those unit actions change an image acquisition region every time acquisition of an image on a predetermined region containing a defect position is completed, and are repeated until a defect-review completion position is reached after starting from a defect-review start position. The magnetic hysteresis removal sequence, that is, a degaussing process is executed at the time of processing in the step of "transfer to a reference position" and in the step of "transfer to a defect position", shown in FIG. 3.

Figure 4:
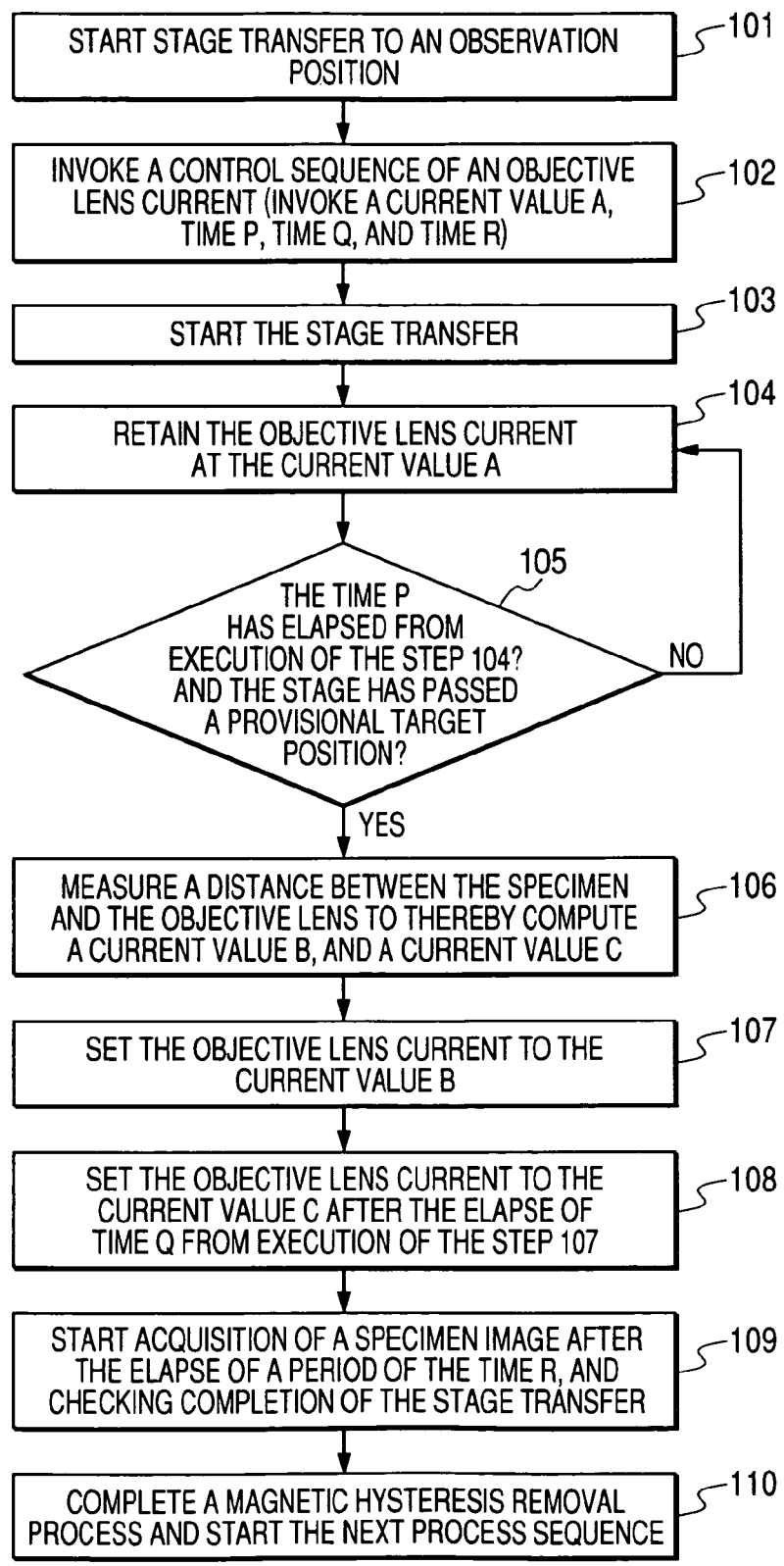
FIG. 4 is a flow chart showing the steps of a magnetic hysteresis removal process according to the invention.

FIG. 4 is a flow chart showing in detail the steps of the degaussing process in FIG. 3. There are described hereinafter details of the magnetic hysteresis removal sequence at the time of transfer accompanied with transfer of the specimen stage, and flow of image acquisition and image retention with reference to FIG. 4.

Upon start of the step of "transfer to a reference position", or the step of "transfer to a defect position", shown in FIG. 3, stage transfer to an observation position, shown in FIG. 4 (step 101), is executed. The step 101 is started upon input of, for example, a command for the stage transfer. Immediately after execution of the step 101, invoking of a control sequence for an objective lens current is executed (step 102), thereby invoking a current value A, time P, time Q, and time R. The current value A is an initial value of an excitation current applied to the objective lens at the time of starting execution of the degaussing process, and is directly and exclusively decided against conditions of energy of the primary electron beam 1 emitted from the electron source 11, a voltage applied to the specimen 17, and so forth. The time P is time information for deciding timing for reading a measured value of the Z-sensor. The time Q is retention time of an overshoot current or an undershoot current. The overshoot current or the undershoot current will be described in detail with reference to FIGS. 5, and 6. The time R is retention time of a final value of the excitation current applied to the objective lens in the flow of the degaussing process, being a value directly and exclusively dependent on dimensions of a field of view for an image displayed on the display device 32, and a set resolution (a set value of a diameter of the primary electron beam 1 on the specimen). Further, the time R corresponds to time from setting of a current value of the objective lens retained at an observation position until dimensions of the primary charged particle beam condensed on the specimen become smaller than dimensions of a field of view per a pixel of a digital image of the specimen at the observation position.

Upon start of the stage transfer (step 103), step 104 is immediately executed, whereupon the objective lens current is retained at the current value A. After execution of the step 104, a site on a transfer path, away by a given distance from a target position of the stage transfer, is set as a provisional target position. Upon setting of the provisional target position, step 105 for determination is executed, thereby determining whether or not the time P has elapsed from a time when the current value A was set, and the stage has passed the provisional target position. In case determination conditions are not met, the step 104 is continuously executed, thereby retaining the objective lens current at the current value A. If the determination conditions are met, computation of a current value B, and a current value C is executed (step 106). In the step 106, the operation unit 31 reads the measured value (the distance between the specimen and the objective lens) of the Z-sensor, thereby working out the retention time Q for the current value B, and the current value C, on the basis of the measured value. For this reason, software for execution of such a computation process as described is stored in the memory 36.

After execution of the step 106, step 107 is executed, whereupon the objective lens current is retained at the current value B for a period of the time Q. Further, after the elapse of the time Q, step 108 is executed, whereupon the objective lens current is retained at the current value C for a period of the time R. Thereafter, the operation unit 31 checks completion of the stage transfer, and subsequently, starts acquisition of a specimen image.

Figure 5:
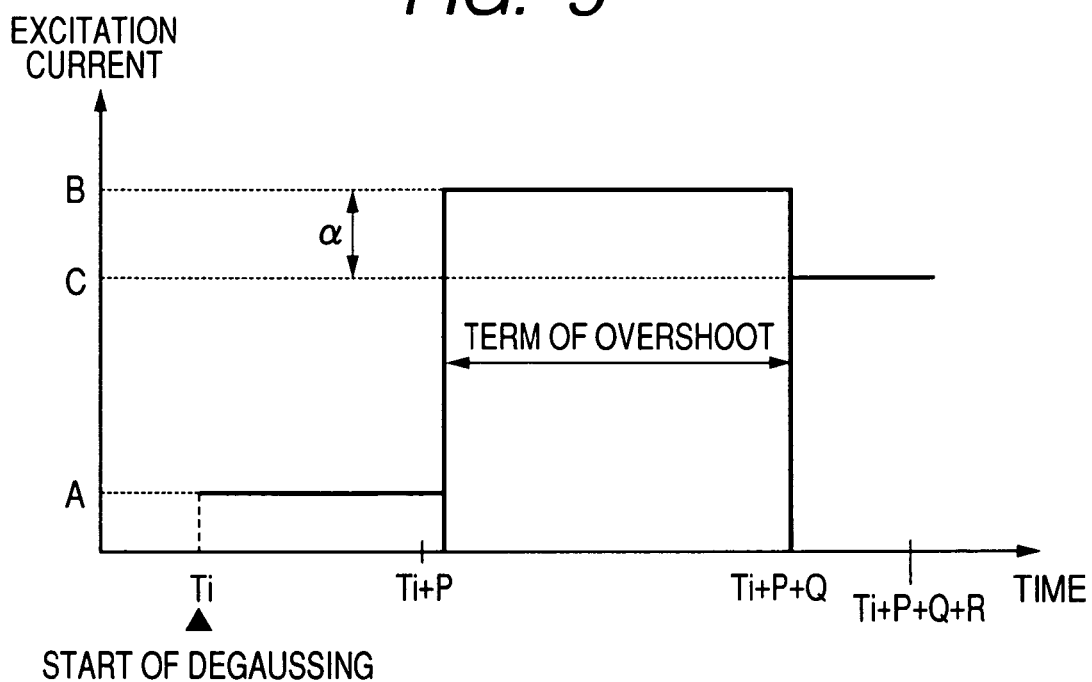
FIG. 5 is a schematic illustration showing an overshoot region of a magnetic lens current according to the invention.
Figure 6:
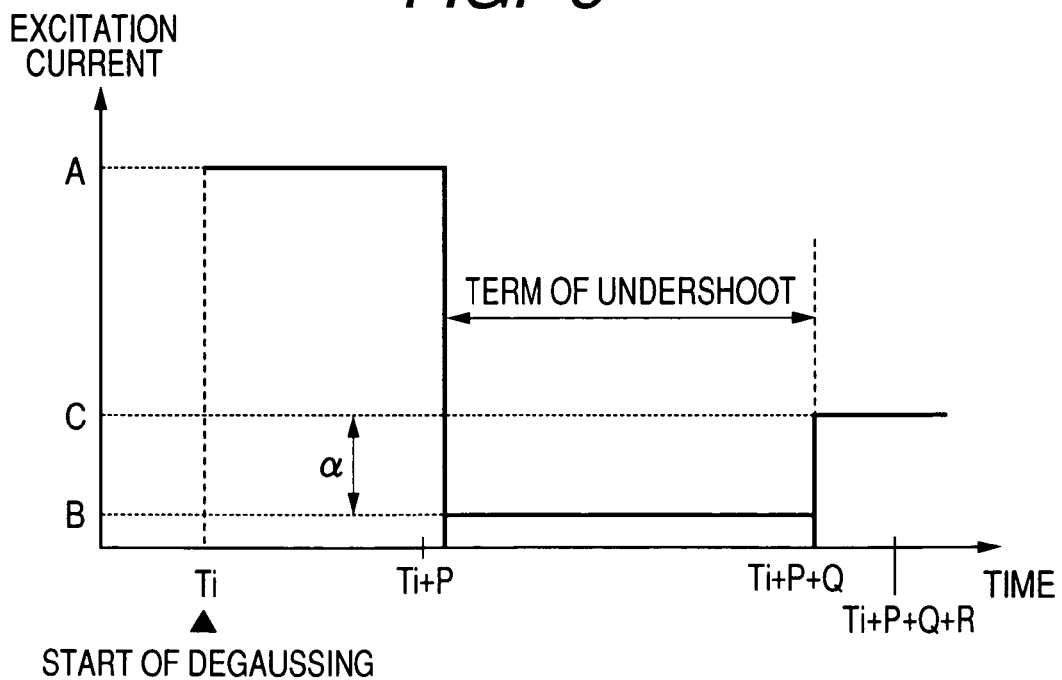
FIG. 6 is a schematic illustration showing an undershoot region of the magnetic lens current according to the invention.

The magnetic hysteresis removal sequence according to the present embodiment has a feature in that a waveform of the excitation current applied to the objective lens is provided with an overshoot region, or an undershoot region. FIG. 5 shows an example of the waveform of the excitation current, having the overshoot region, and FIG. 6 shows an example of the waveform of the excitation current, having the undershoot region. Upon the start of the degaussing process at time Ti after the execution of the step 104 shown in FIG. 4, an excitation current value of the objective lens is set to the initial value A. If the determination conditions are met in the step 105 for determination, the excitation current value of the objective lens is set to an overshoot current value B, or an undershoot current value B to be retained for a period of the time Q. Since a set time of an overshoot current or an undershoot current is after the elapse of the step 105 for determination, some time lag from a time at Ti+P occurs to actual time when the excitation current is set to the current value B. In this connection, with the present embodiment, the current value B is set to a value with a given offset value a added to the current value C. With the elapse of the retention time Q, the excitation current value of the objective lens is set to the final value C to be retained for a period of the time R. Upon completion of the retention time R, the degaussing process is completed.

In the description given hereinabove, the current value C is a current value of the objective lens, at which the primary charged particle beam physically comes to have an optimum beam diameter on the specimen at the observation position, and a relationship of |the current value A|<|the current value C|<|the current value B|, or |the current value B|<|the current value C|<|the current value A| holds in terms of the absolute value of current values. Herein, the current value A, the current value B, and the current value C all are the same in polarity. Accordingly, with the present embodiment, the term "overshoot", and "undershoot" are used in the sense that the excitation current value of the objective lens in a relevant region is greater than the initial value A, and the final value C, respectively, or smaller than the initial value A, and the final value C, respectively.

If the excitation current is caused to pass through the overshoot region, or the undershoot region once in a period during which the excitation current value is caused to change from the initial value A to the final value C, this will lower an eddy current value rising in the objective lens due to a change in the excitation current, so that it is possible to obtain an advantageous effect in that variation in dimensions of the primary charged particle beam condensed on the specimen is rapidly converged.

With the examples of configuration, described with reference to FIGS. 5, and 6, respectively, the retention time of the current value A is time until a time when the time P has elapsed, and the stage has passed the provisional target position, however, the retention time of the current value A may be controlled so as to coincide with the time P all the time. Further, the waveform of the excitation current is divided into two regions for a period from the start of the degaussing until a time when the final value C is reached, however, the waveform of the excitation current may be divided into three or more regions, and it need only be sufficient for the excitation current value to contain a value greater than, or smaller than the absolute value of the optimum current value (that is, the overshoot region, or the undershoot region).

Figure 7:
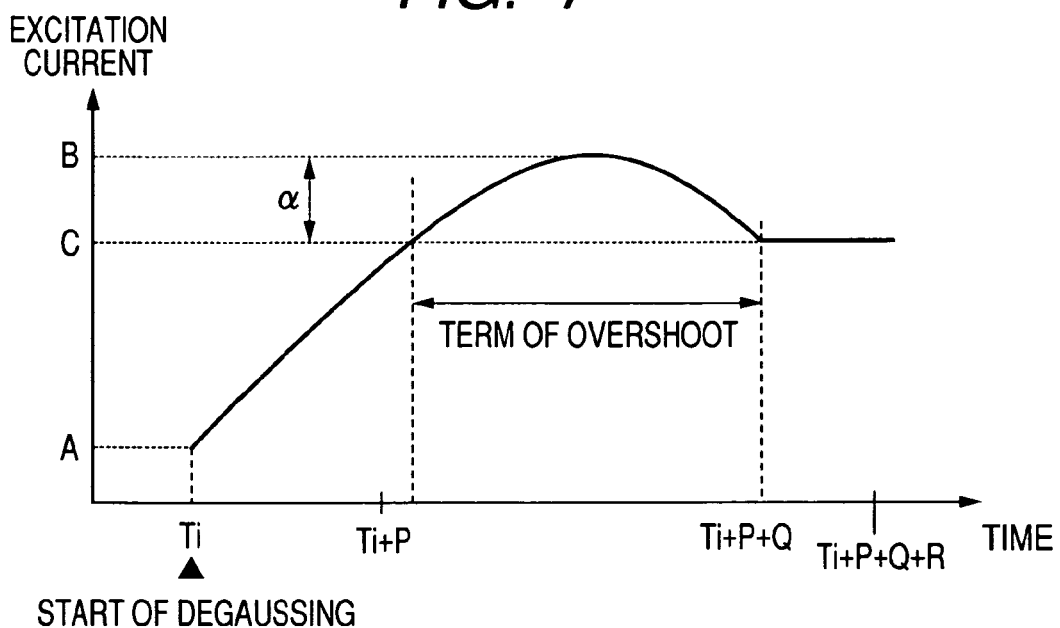
FIG. 7 is a schematic illustration showing an overshoot region of another magnetic lens current according to the invention.
Figure 8:
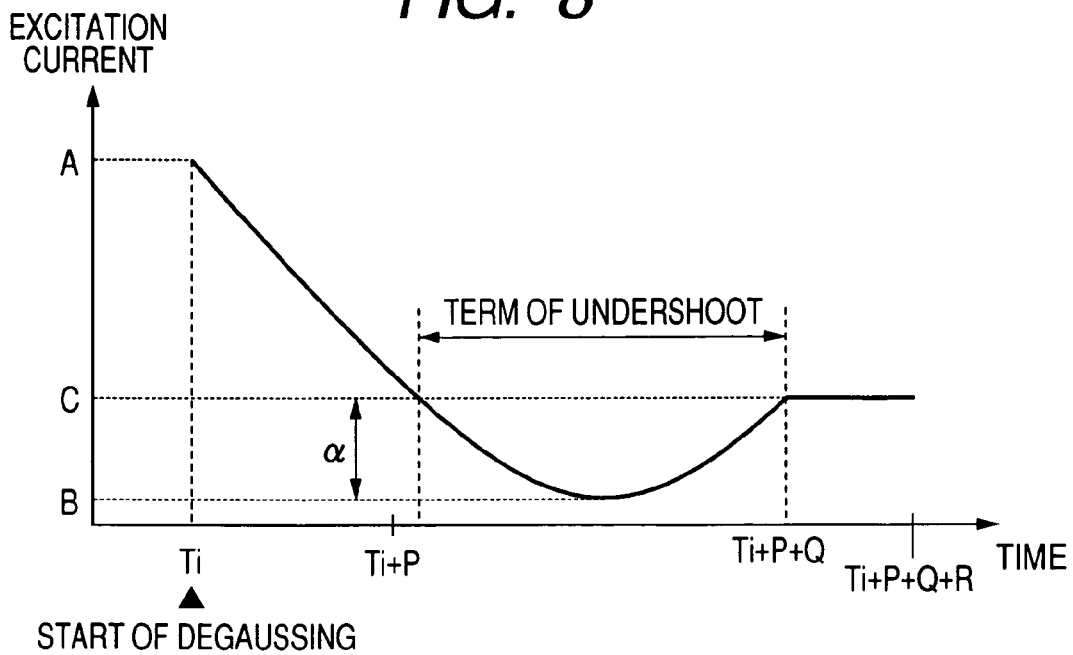
FIG. 8 is a schematic illustration showing an undershoot region of another magnetic lens current according to the invention.

FIGS. 7 and 8 each show an example of another configuration of a waveform of an excitation current. The waveforms of the excitation current, shown in FIGS. 7, and 8, respectively, represent an example of a configuration wherein the waveform of the excitation current is caused to undergo continuous variation from an initial value A to a final value C, still passing through an overshoot region, or an undershoot region. In this case, a maximum excitation current value in the overshoot region, or a minimum excitation current value in the undershoot region corresponds to the current value B, which is set by offsetting against the final value C. Time P, and time Q can be set in a manner similar to the case of the examples of the configuration, shown in FIGS. 5, and 6, respectively.

Thus, with the present embodiment, even if there occurs a change in the setting conditions of the objective lens, accompanying transfer to the observation position, repeatability of the magnetic field produced by the magnetic lens, against current applied to the electromagnetic coil, is enhanced, so that a defect-review system capable of acquiring a sharp image with shorter latency time than before has been implemented. Furthermore, the configurations according to the present embodiment are applicable not only to the defect-review system but also to a size measurement system for a semiconductor circuit, and various types of interconnections.

Second Embodiment

Figure 9:
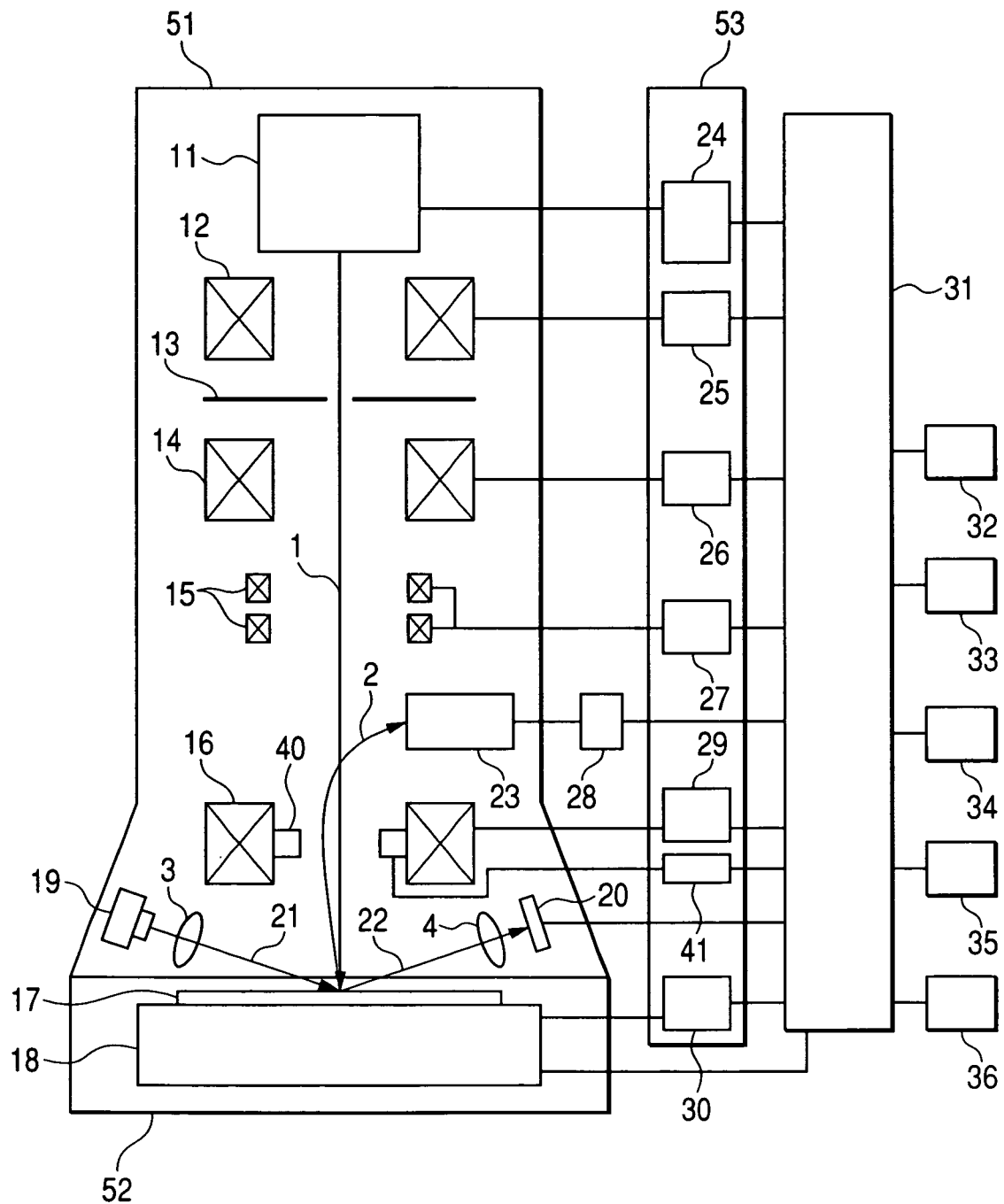
FIG. 9 is a schematic block diagram of another charged particle beam apparatus according to the invention.

As a second embodiment, there is described hereinafter a configuration of a defect-review system wherein an electrostatic lens is overlaid on an objective lens. FIG. 9 is a schematic block diagram of the defect-review system according to the present embodiment. Description of constituent elements in the figure, equivalent to those in FIG. 1, in respect of action•function, is omitted. With the defect-review system shown in FIG. 9, lens action of an electrostatic lens 40 is superimposed on lens action of an objective lens 16 according to an instruction of an operation unit 31. Pre-recorded in a memory 36 at this point in time is time-dependent change in beam diameter, or time-dependent change in a magnetic field produced by the objective lens after setting of a current value of the objective lens, at which the primary charged particle beam comes to have an optimum beam diameter on a specimen at an observation position, at the time of a change in conditions of the objective lens, accompanied with transfer of the observation position, and an operation unit 31 can read information thereon. The configuration of the present embodiment, in other respects, is the same as that of the first embodiment, omitting therefore description thereof.

With the present configuration, in the case of executing the magnetic hysteresis removal sequence at the time of transfer accompanied with transfer of the specimen stage, as described in the first embodiment, the electrostatic lens 40 is actuated after the current value C is set in such a way as to compensate for the time-dependent change in the magnetic field produced by the objective lens 16, so that the primary charged particle beam can always have an optimum beam diameter on the specimen, thereby enabling time required for acquisition of an image to be further shortened. Further, it goes without saying that the same effect as that of the electrostatic lens 40 may be obtained by causing a specimen voltage control power supply source 30 to vary a voltage applied to the specimen 17. Furthermore, as is the case with the first embodiment, the configuration according to the present embodiment is applicable not only to the defect-review system but also to a size measurement system for a semiconductor circuit, and various types of interconnections.

Third Embodiment

Figure 10:
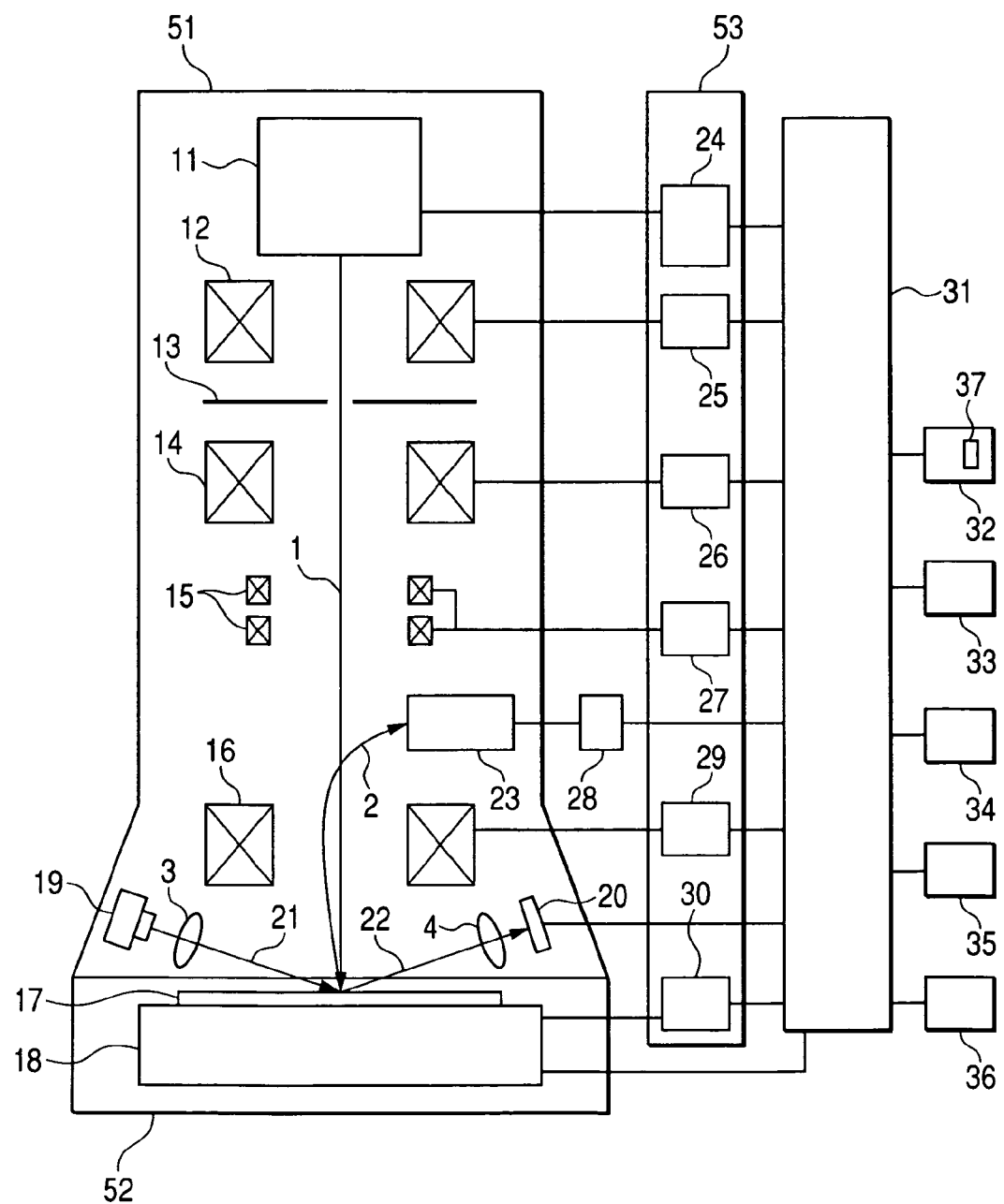
FIG. 10 is a schematic block diagram of still another charged particle beam apparatus according to the invention.
Figure 11:
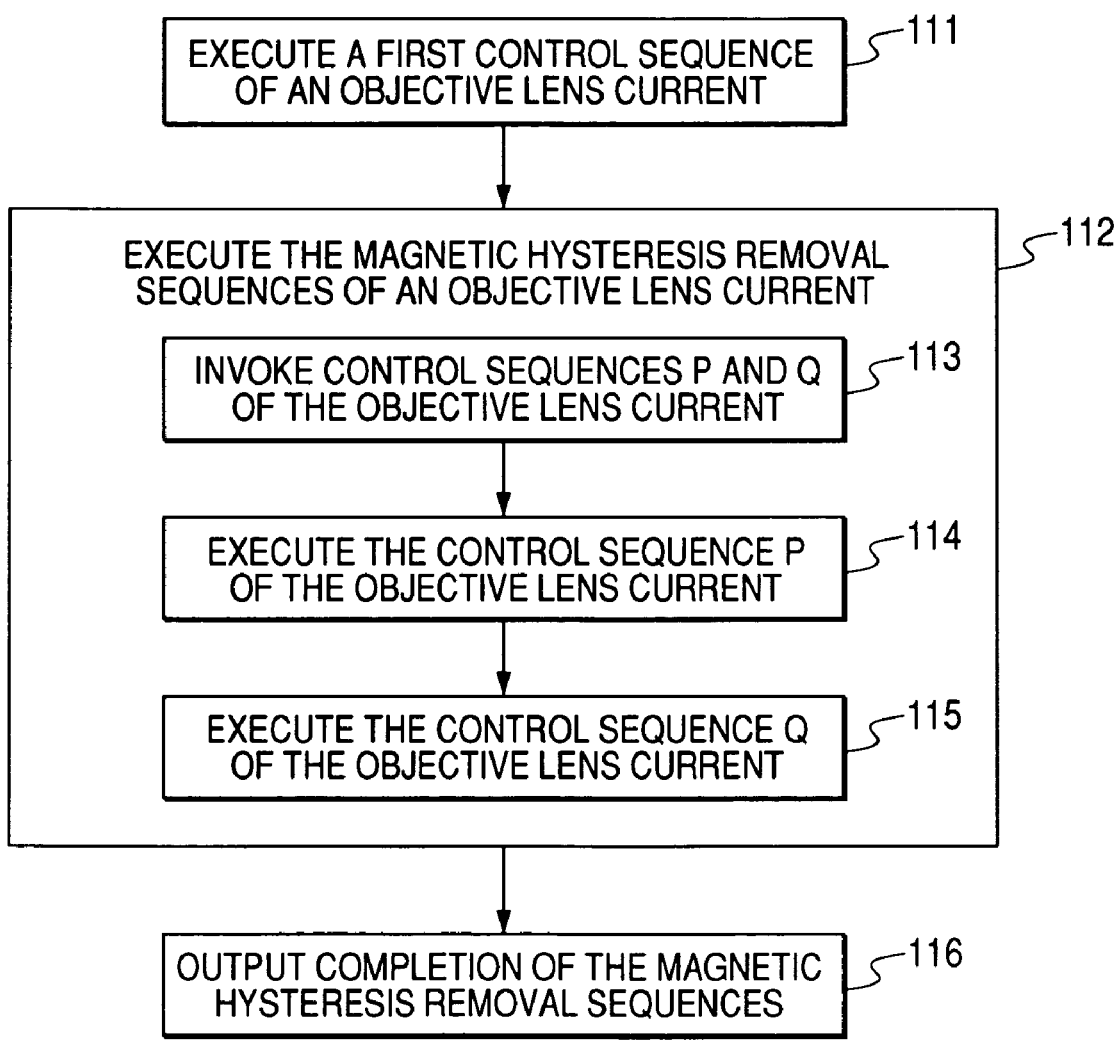
FIG. 11 is a flow chart showing the steps of another magnetic hysteresis removal process according to the invention.

As a third embodiment, there is described hereinafter an embodiment of a defect-review system mounted with a function for removal of magnetic hysteresis in the case of deterioration in repeatability of the magnetic field produced by the magnetic lens upon application of current to the electromagnetic coil during execution of the first embodiment. FIG. 10 is a schematic block diagram of a scanning electron microscope according to the present embodiment. Constituent elements within an electron beam column 51, a specimen chamber 52, and a power supply unit 53, respectively, are the same in respect of action function as those corresponding thereto, in the configuration shown in FIG. 1, omitting therefore description thereof. With the scanning electron microscope shown in FIG. 10, a start button (degauss button) 37 for removal of magnetic hysteresis is displayed as GUI on a display device 32, and a magnetic hysteresis removal sequence is executed by clicking the degauss button 37. Otherwise, a start command for the magnetic hysteresis removal sequence may be directly imputed via an input unit 35.

When start of a degaussing process is instructed through operation of the degauss button 37, or command input (step 111), an apparatus is changed over into an execution mode for the magnetic hysteresis removal sequence, and thereafter, magnetic hysteresis removal sequences of an objective lens current is executed (step 112). Herein, in the step 112 for the magnetic hysteresis removal sequences for the objective lens current, there are executed step 113 for invoking control sequences of the objective lens current, step 114 for execution of a control sequence P of the objective lens current, and step 115 for execution of a control sequence Q of the objective lens current. Decision on respective control values of a current value, and time, executed in the control sequence Q of the step 115, is made by the same method as a method for deciding the values as set in the first embodiment. In the control sequence P of the step 114, there will be no problem whichever sequence may be executed provided that a current value greater than a maximum current value, or smaller than a minimum current value of current set in the step 115 is given as a set current value. As a result of execution of the step 114, the magnetic hysteresis that cannot be removed by the magnetic hysteresis removal sequence executed in the first embodiment is reduced to magnetic hysteresis that can be removed by the sequence executed by the step 115. After completion of the step 113 for execution of second control sequence of the objective lens current, there is executed step 116 for outputting completion of the magnetic hysteresis removal sequences, whereupon the apparatus will be in operable state for acquisition and retention of an image. Further, since computation of the current value, executed in the step 115, is not accompanied with transfer of the stage, the same may be executed at the time of execution of either the step 113, or the step 115.

With the present embodiment, even in the case of deterioration in repeatability of the magnetic field produced by the magnetic lens upon application of current to the electromagnetic coil, it is possible to implement a scanning electron microscope capable of restoring the repeatability, and acquiring sharp images. Furthermore, as is the case with the first embodiment, the advantageous effects of the present embodiment can be exhibited even when the configuration according to the present embodiment is applied not only to a defect-review system but also to a size measurement system for a semiconductor circuit, and various types of interconnections.

Fourth Embodiment

Figure 12:
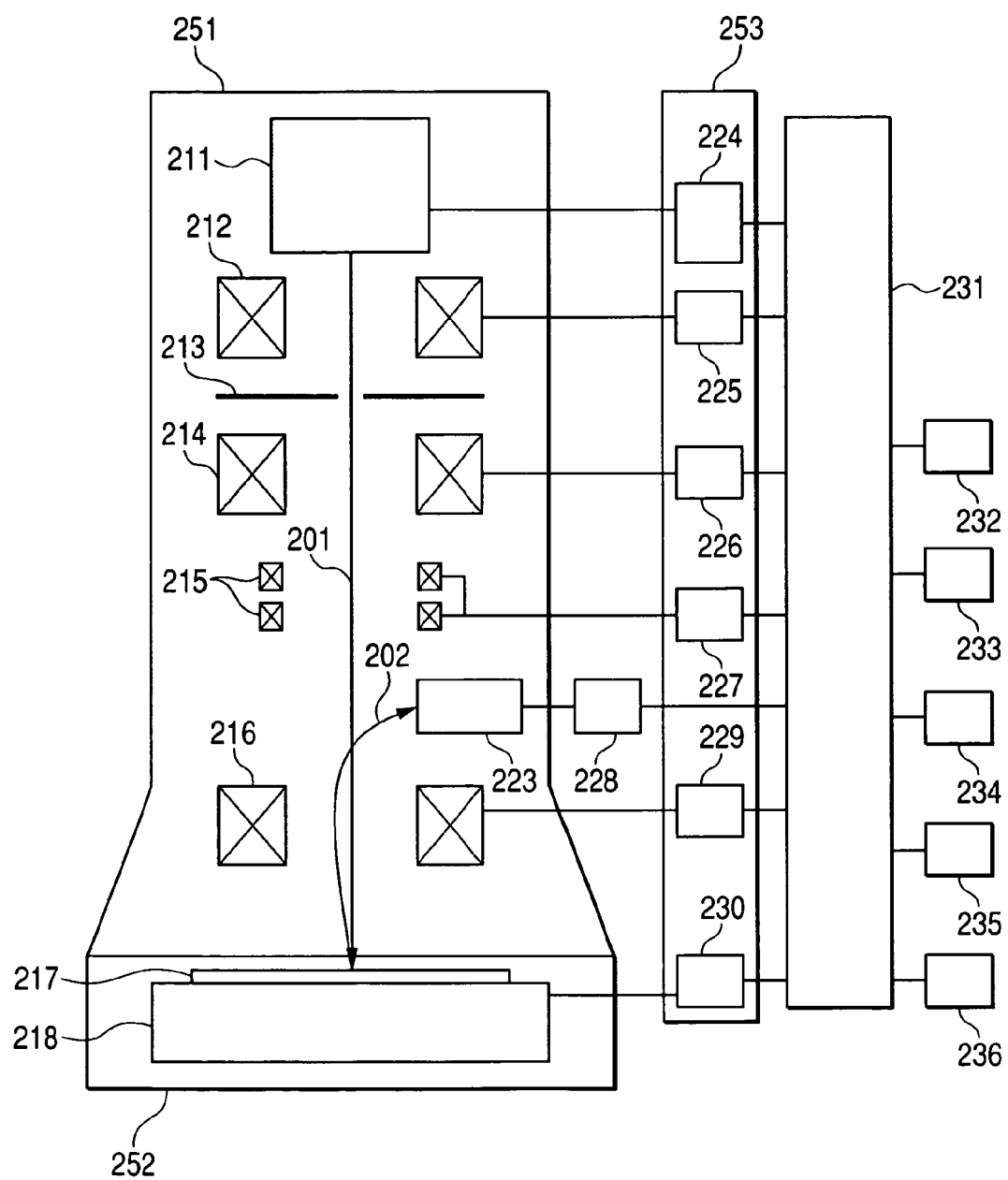
FIG. 12 is a schematic block diagram of yet another charged particle beam apparatus according to the invention.

As a fourth embodiment, there is described hereinafter an example of a configuration of a scanning electron microscope equipped with a function for high-speed changeover of a probe current of a primary electron beam by use of a magnetic lens. FIG. 12 is a schematic block diagram of a scanning electron microscope according to the present embodiment.

As in the respective cases of the embodiments 1 to 3, the scanning electron microscope shown in FIG. 12 comprises an electron beam column 251, a specimen chamber 252, a power supply unit 253, an operation unit 231, and accessory constituent elements thereof. A primary electron beam 201 emitted from an electron source 211 controlled by a high-voltage control power source 224 has a crossover position thereof adjusted by a first condenser lens 212 controlled by a lens control power source 225, and passes through an aperture 213, whereupon a beam current amperage is restricted to a predetermined value. The primary electron beam 201 with the current amperage as adjusted is condensed into a minute spot on a specimen 217 by a second condenser lens 214 controlled by a lens control power source 226, and by an objective lens 216 controlled by an objective lens control power supply source 229. Further, the primary electron beam 201 is caused to two-dimensionally scan on the specimen according to a size of a scanning region, and scanning speed by a deflector 215 controlled by a deflector control power supply source 227. When a voltage controlled by a specimen control power supply source 230 is applied to the specimen 217, the specimen 17 is irradiated with the primary electron beam 201 at reduced speed. A secondary signal 202 that consists of a secondary electron, and so forth, generated from the specimen 217, upon irradiation thereof with the primary electron beam 201, is detected by a secondary signal detector 223. The signal detected by the secondary signal detector 223 is amplified by a signal amplifier 228 to be subsequently transferred to an image memory 233, whereupon a specimen image is displayed on a display device 232. Operation of the scanning electron microscope, described as above, is controlled by the operation unit 231 reading control software stored in a memory 236 to thereby control respective output values of various control power sources included in the power supply unit 253.

With the present embodiment, the high-speed changeover of the probe current is implemented by changing condensation conditions of the first condenser lens 212 to thereby varying a proportion of unnecessary regions of the primary electron beam, to be removed by the aperture 213. At this point in time, condensation conditions of the second condenser lens 214 is changed in association with a change in the condensation conditions of the first condenser lens 212 so as not to cause a change in condensation conditions of the objective lens 216. Information on magnetic hysteresis removal sequences to be executed before setting to the current values and condensation conditions for the respective lenses after the change in the respective condensation conditions of the first condenser lens 212, and the second condenser lens 214 is pre-stored in the memory 236.

Figure 13:
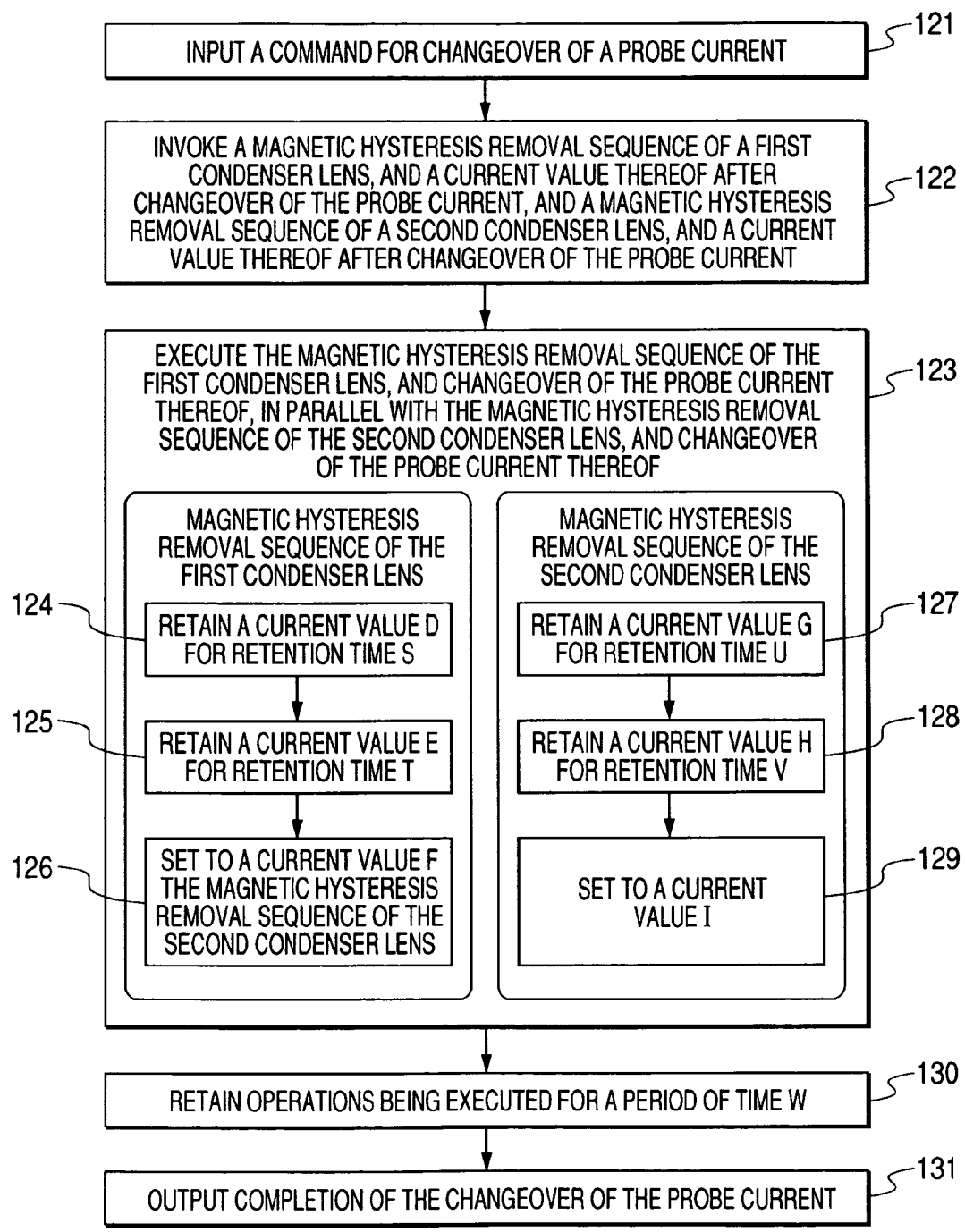
FIG. 13 is a flow chart showing the steps of still another magnetic hysteresis removal process according to the invention.

There is described hereinafter flow of the magnetic hysteresis removal sequences according to the present embodiment with reference to FIG. 13. Upon inputting of a command for changeover of a probe current (step 121), the magnetic hysteresis removal sequence of the first condenser lens, and a current value thereof after changeover of the probe current, and the magnetic hysteresis removal sequence of the second condenser lens, and a current value thereof after changeover of the probe current are invoked (step 122). Invoked from the memory 236 are parameters of the magnetic hysteresis removal sequence of the first condenser lens, that is, a current value D, a current value E, time S, Time T, and a current value F of the first condenser lens after the changeover of the probe current, parameters of the magnetic hysteresis removal sequence of the second condenser lens, that is, a current value G, a current value H, time U, time V, a current value I of the second condenser lens after the changeover of the probe current, and time W. The current value D, current value E, the time S, and the time T are directly exclusively decided by a value of the current value F while the current value G, current value H, the time U, the time V are directly exclusively decided by a value of the current value I.

In step 123, a changeover flow of the magnetic hysteresis removal sequence of the first condenser lens, and the probe current thereof are executed in parallel with a changeover flow of the magnetic hysteresis removal sequence of the second condenser lens, and the probe current thereof. Upon start of the step 123, the first condenser lens 212, and the second condenser lens 214 independently execute the following actions, respectively. With the first condenser lens 212, step 124 for retaining an initial current value (the current value: D, the retention time: S), step 125 for retaining an overshoot (or undershoot) current (the current value: E, the retention time: T), and step 126 for setting to a final current value F are sequentially executed. Similarly, with the second condenser lens 214, step 127 for retaining an initial current value (the current value: G, the retention time: U), step 128 for retaining an overshoot (or undershoot) current (the current value: H, the retention time: V), and step 129 for setting to a final current value I are sequentially executed. Upon completion of the step 126, and the step 129, step 130 for retention is executed, thereby retaining state of excitation with the final current value F, or the final current value I for a period of the time W. In this case, the time W corresponds to time from completion of the both the step 126, and the step 129 until dimensions of a primary charged particle beam condensed on the specimen become smaller than dimensions of a field of view per a pixel of a digital image of the specimen at an observation position, the time W being found by computation beforehand. Thereafter, step 131 for outputting completion of the changeover of the probe current is executed and the apparatus will be in operable state for acquisition and retention of an image.

With the present embodiment, there has been implemented a scanning electron microscope capable of executing high-speed changeover of a probe current while maintaining sharpness in acquired images.

With the embodiments 1 to 4, respectively, there have been described hereinabove the examples of respective configurations of the defect-review system, and the scanning electron microscope, however, it is to be pointed out that the invention is applicable not only to the scanning electron microscope but also to various charged particle beam apparatuses such as a transmission electron microscope, an ion beam system, and so forth. Thus, by applying the invention to a charged particle beam apparatus employing magnetic lens unit, it becomes possible to change over a value of current applied to the magnetic lens unit while maintaining high picture quality of an acquired image, thereby implementing a high performance charged particle beam apparatus wherein the high picture quality of the acquired image is compatible with high acquisition speed.

What is claimed is:

1. A charged particle beam apparatus comprising:
   a specimen chamber containing a specimen stage for holding a specimen; a charged particle beam column for scanning on the specimen with a primary charged particle beam, and detecting a secondary particle generated from the specimen to thereby output results of detection in the form of an output signal; and the charged particle beam column comprising:
   a magnetic lens unit for causing a magnetic field excited by current to act on the primary charged particle beam;
   a control power supply source for executing a process for reducing magnetic hysteresis present in the magnetic lens unit by supplying the magnetic lens unit with excitation current of a predetermined magnitude for a predetermined time only; and
   an operation unit for stopping the process for reducing the magnetic hysteresis at a point in time when a diameter of a spot of the primary charged particle beam, on the specimen, becomes smaller than a set value.

2. A charged particle beam apparatus comprising:
   a specimen chamber containing a specimen stage for holding a specimen; and a charged particle beam column for scanning on the specimen with a primary charged particle beam, and detecting a secondary particle generated from the specimen to thereby output results of detection in the form of an output signal, the charged particle beam column comprising:
   a magnetic lens unit for causing a magnetic field excited by current to act on the primary charged particle beam;
   a control power supply source for executing a process for reducing magnetic hysteresis present in the magnetic lens unit by supplying the magnetic lens unit with excitation current of a predetermined magnitude for a predetermined time; and
   an operation unit for controlling the excitation current such that the excitation current supplied by the magnetic lens unit at the time of the process for reducing the magnetic hysteresis is provided with an overshoot region where an excitation current value is greater than either an initial value or the excitation current or a final value thereof, or an undershoot region where the excitation current value is smaller than either the initial value or the final value between the initial value and the final value.

3. The charged particle beam apparatus according to claim 1, wherein the operation unit executes the process for reducing the magnetic hysteresis while a measurement position on the specimen is executed while a measurement position on the specimen is transferred toward an irradiation position of the primary charged particle beam as condensed.

4. The charged particle beam apparatus according to claim 2, wherein the operation unit executes the process for reducing the magnetic hysteresis while a measurement position on the specimen is executed while a measurement position on the specimen is transferred toward an irradiation position of the primary charged particle beam as condensed.

5. The charged particle beam apparatus according to claim 2, wherein the operation unit controls the excitation current such that if the overshoot region exists in the excitation current, the absolute value of the final value is greater than the absolute value of the initial value of the excitation current, and if the undershoot region exists in the excitation current, the absolute value of the final value is smaller than the absolute value of the initial value of the excitation current.

6. The charged particle beam apparatus according to claim 1, wherein the operation unit controls the excitation current such that a waveform of the excitation current applied to the magnetic lens unit at the time of the process for reducing the magnetic hysteresis is formed seas to be divided into three stages including an initial region, a maximum excitation current region, or a minimum excitation current region, and a final region.

7. The charged particle beam apparatus according to claim 2, wherein the operation unit controls the excitation current such that a waveform of the excitation current applied to the magnetic lens unit at the time of the process for reducing the magnetic hysteresis is formed so as to be divided into three stages including an initial region, a maximum excitation current region, or a minimum excitation current region, and a final region.

8. The charged particle beam apparatus according to claim 1, further comprising a height measuring device for measuring a height of the specimen, wherein a value of the excitation current applied to the magnetic lens unit upon completion of the process for reducing the magnetic hysteresis is decided according to a measurement value of the height measuring device.

9. The charged particle beam apparatus according to claim 2, further comprising a height measuring device for measuring a height of the specimen, wherein the final value of the excitation current is decided according to a measurement value of the height measuring device.

10. The charged particle beam apparatus according to claim 9, wherein the operation unit executes reading of measurement results of the height measuring device before the excitation current value reaches a maximum value in the overshoot region, or a minimum value in the undershoot region.

11. The charged particle beam apparatus according to claim 9, wherein the operation unit sets a maximum excitation current value in the overshoot region, or a minimum excitation current value in the undershoot region is a value with a predetermined offset value added to the final value of the excitation current.

12. The charged particle beam apparatus according to claim 1, wherein the magnetic lens unit comprise a magnetic lens.

13. The charged particle beam apparatus according to claim 12, wherein the magnetic lens unit further comprise an electrostatic lens.

14. The charged particle beam apparatus according to claim 1, wherein the charged particle beam column comprises an electron gun, objective lens, and condenser lenses, and the magnetic lens unit are the condenser lenses.

15. The charged particle beam apparatus according to claim 1, wherein the operation unit executes a second process for reducing magnetic hysteresis, differing from the process for reducing the magnetic hysteresis, prior to execution of the process for reducing the magnetic hysteresis.

16. The charged particle beam apparatus according to claim 15, further comprising a display device for displaying operation results of the operation unit, wherein if the process for reducing the magnetic hysteresis fails to meet a predetermined effect, an execution button for the second process for reducing magnetic hysteresis is displayed on the display device, and the second process for reducing magnetic hysteresis is executed by clicking the execution button.

17. The defect-review system according to claim 1, wherein the operation unit executes the process for reducing the magnetic hysteresis while the specimen stage is being transferred.

18. A defect-review system for acquiring a scanning electron beam image on the basis of information on a position of a defect existing on a semiconductor wafer, said defect review system comprising:

a specimen platform for holding the semiconductor wafer;

a scanning electron microscope for scanning a region containing the position of the defect with a primary electron beam to thereby acquire the scanning electron beam image;

a specimen stage for transferring the specimen platform in order to transfer the position of the defect to an irradiation position of the primary charged particle beam; and a display device for displaying the scanning electron beam image, wherein the scanning electron microscope includes:

a magnetic lens unit for causing a magnetic field excited by an excitation current to act the primary charged particle beam;

a power supply unit for executing a process for reducing magnetic hysteresis present in the magnetic lens unit by supplying the magnetic lens unit with excitation current of a predetermined magnitude for a predetermined time only; and an operation unit for stopping the process for reducing the magnetic hysteresis at appoint in time when a diameter of a spot of the primary charged particle beam becomes smaller than a resolution required of data on the scanning electron beam image.

\* \* \* \* \*